US012683165B2

(12) United States Patent
Kim et al.

(10) Patent No.: US 12,683,165 B2
(45) Date of Patent: Jul. 14, 2026

(54) POSITIVE ELECTRODE ADDITIVE FOR LITHIUM SECONDARY BATTERY, POSITIVE ELECTRODE ACTIVE MATERIAL COMPRISING SAME, POSITIVE ELECTRODE, AND LITHIUM SECONDARY BATTERY

(71) Applicant: LG ENERGY SOLUTION, LTD., Seoul (KR)

(72) Inventors: Bong Soo Kim, Daejeon (KR); Taek Gyoung Kim, Daejeon (KR); Kee Yoon Lee, Daejeon (KR); Kangho Cheon, Daejeon (KR); Hee Jung Park, Daejeon (KR)

(73) Assignee: LG Energy Solution, Ltd., Seoul (KR)

( * ) Notice: Subject to any disclaimer, the term of this patent is extended or adjusted under 35 U.S.C. 154(b) by 601 days.

(21) Appl. No.: 18/028,701

(22) PCT Filed: Jan. 6, 2022

(86) PCT No.: PCT/KR2022/000235
§ 371 (c)(1),
(2) Date: Mar. 27, 2023

(87) PCT Pub. No.: WO2022/149878
PCT Pub. Date: Jul. 14, 2022

(65) Prior Publication Data

US 2023/0361302 A1 Nov. 9, 2023

(30) Foreign Application Priority Data

Jan. 7, 2021 (KR) ........................ 10-2021-0001836
Jan. 12, 2021 (KR) ........................ 10-2021-0004278

(51) Int. Cl.
*H01M 4/62* (2006.01)
*C07D 209/56* (2006.01)
(Continued)

(52) U.S. Cl.
CPC ............ *H01M 4/62* (2013.01); *C07D 209/56* (2013.01); *H01M 4/38* (2013.01); *H01M 4/583* (2013.01);
(Continued)

(58) Field of Classification Search
CPC .... H01M 4/62; H01M 4/583; H01M 10/0525; C07D 209/56
(Continued)

(56) References Cited

U.S. PATENT DOCUMENTS 5,986,099 A 11/1999 Mullen et al.
2010/0181527 A1 7/2010 Nesvadba et al.
(Continued)

FOREIGN PATENT DOCUMENTS

CN 101184825 A 5/2008
CN 107851776 A 3/2018
(Continued)

OTHER PUBLICATIONS

Rao, K. & George, S. (2010). "Synthesis and Controllable Self-Assembly of a Novel Coronene Bisimide Amphiphile". Organic Letters, 12(11), 2656-2659 (Year: 2010).*
(Continued)

*Primary Examiner* — Allison Bourke
*Assistant Examiner* — Robert Gene West
(74) *Attorney, Agent, or Firm* — Bryan Cave Leighton Paisner LLP

(57) ABSTRACT

The present disclosure relates to a positive electrode additive for a lithium secondary battery, and a positive electrode active material, a positive electrode and a lithium secondary battery including the same, and in particular, the positive electrode additive represented by Formula 1 is formed on a surface of a carbon material included in the positive electrode active material and is not dissolved in an electrolyte
(Continued)

solution, which functions to electrically separate the positive electrode and a negative electrode, and accordingly, battery performance is enhanced by suppressing side reactions in the battery.

13 Claims, 4 Drawing Sheets

(51) Int. Cl.

| | |
|---|---|
| ***H01M 4/02*** | (2006.01) |
| ***H01M 4/38*** | (2006.01) |
| ***H01M 4/583*** | (2010.01) |
| ***H01M 10/0525*** | (2010.01) |
| ***H01M 10/056*** | (2010.01) |

(52) U.S. Cl.
CPC .. *H01M 10/0525* (2013.01); *H01M 2004/021* (2013.01); *H01M 10/056* (2013.01); *H01M 2300/0028* (2013.01)

(58) Field of Classification Search
USPC ........................................................ 429/231.8
See application file for complete search history.

(56) References Cited

U.S. PATENT DOCUMENTS

| | | | |
|---|---|---|---|
| 2011/0149393 | A1 | 6/2011 | Nokel et al. |
| 2017/0222226 | A1 | 8/2017 | Helms et al. |
| 2017/0263932 | A1 | 9/2017 | Kumakura et al. |
| 2018/0241076 | A1 | 8/2018 | Nishiura et al. |
| 2019/0067682 | A1 | 2/2019 | Cho et al. |
| 2021/0151757 | A1 | 5/2021 | Kim et al. |

FOREIGN PATENT DOCUMENTS

| | | | |
|---|---|---|---|
| IN | IN/PCT/2007/07250 | | 12/2007 |
| JP | H11-502546 | A | 3/1999 |
| JP | 2011-513376 | A | 4/2011 |
| JP | 2013-191328 | A | 9/2013 |
| JP | WO2016/021483 | A1 | 2/2016 |
| KR | 10-2018-0017724 | A | 2/2018 |
| KR | 10-2020-0033737 | A | 3/2020 |
| WO | 2021/142444 | A2 | 7/2021 |

OTHER PUBLICATIONS

Gerber et al.,(2016) “Three-Dimensional Growth of Li2S in Lithium-Sulfur Batteries Promoted by a Redox Mediator”, Nano Lett., 16, 1, pp. 549-554.
Kim, et al., (2020) “New Redox-Mediating Polymer Binder For Enhancing Performance of Li—S Batteries”, Journal of Energy Chemistry, vol. 44, pp. 154-161.
Cole et al., (2020) “Organocatalyzed Birch Reduction Driven by Visible Light”, J. Am. Chem. Soc., 142, 31, pp. 13573-13581.
Manning et al., (2011) “Synthesis, Characterization, and Photophysical Study of Fluorescent N-substituted Benzo[ghi]perylene “Swallow Tail” Monoimides”, J. Org. Chem, 76, pp. 6007-6013.
Hirayama et al. “Systematic Control of the Excited-State Dynamics and Carrier-Transport Properties of Functionalized Benzo[ghi]perylene and Coronene Derivatives,” Chem. Eur. J. 2014, 20, 9081-9093.
Rao et al. “Synthesis and Controllable Self-Assembly of a Novel Coronene Bisimide Amphipile,” Organic Letters 2010, vol. 12, No. 11 2656-2659.

* cited by examiner

【Figure 1】
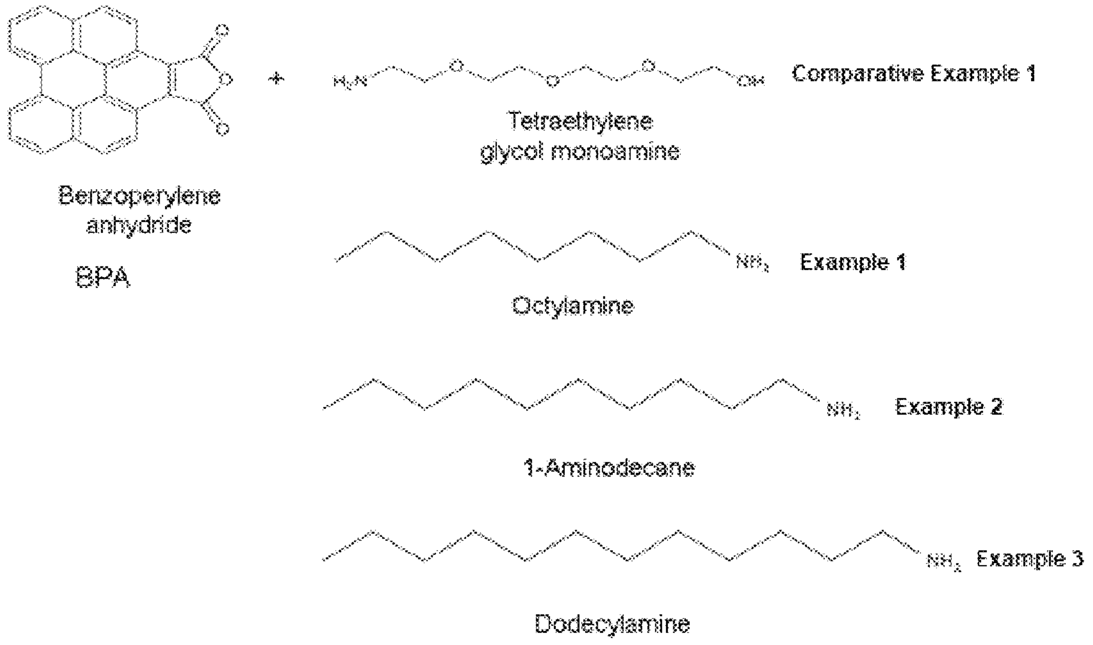
Benzoperylene anhydride
BPA
+
Tetraethylene glycol monoamine Comparative Example 1
Octylamine Example 1
1-Aminodecane Example 2
Dodecylamine Example 3
【Figure 2】
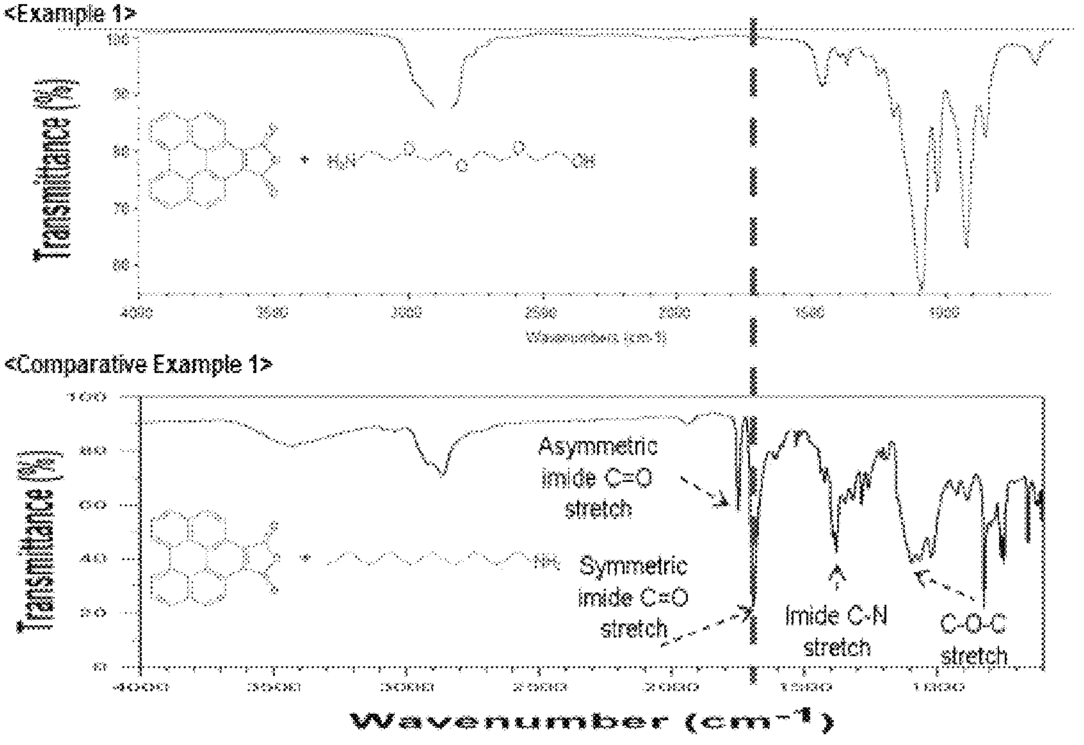

【Figure 3】
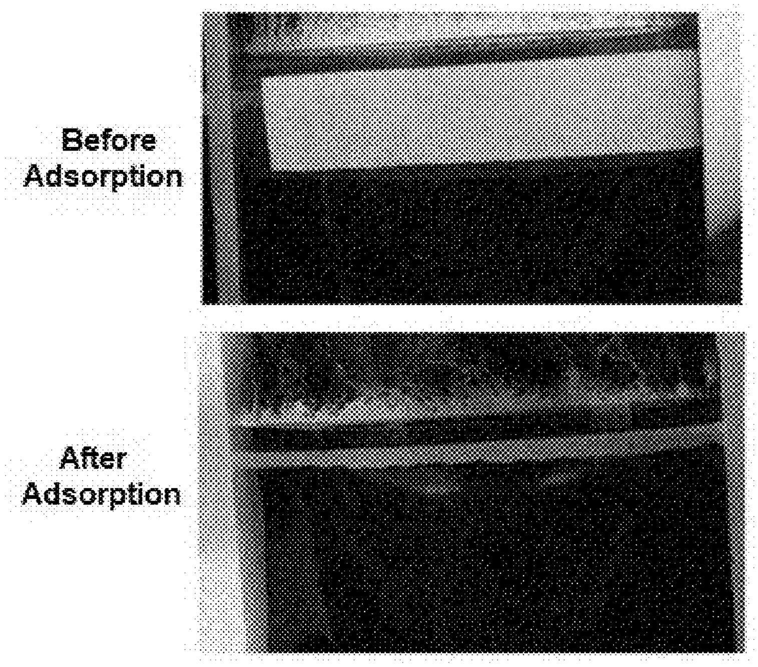
【Figure 4】
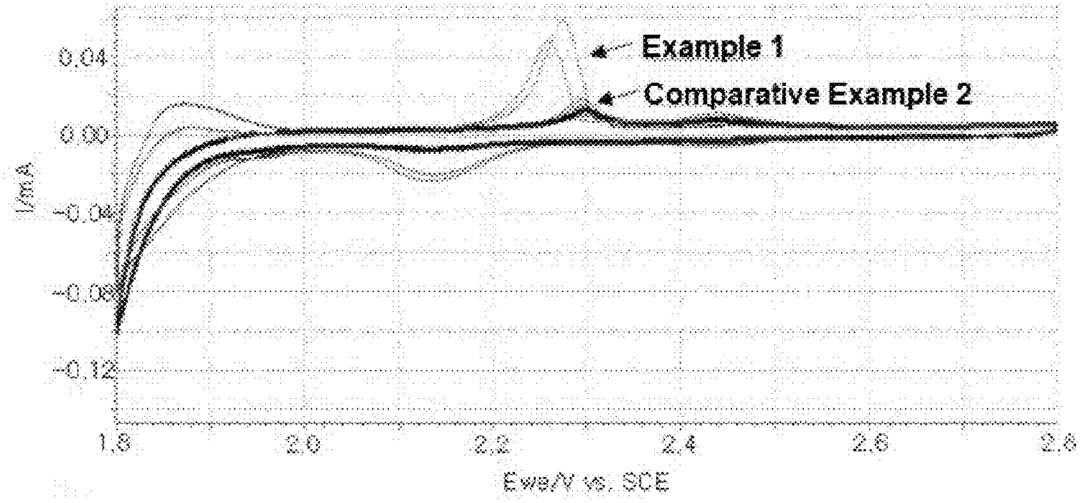

【Figure 5】
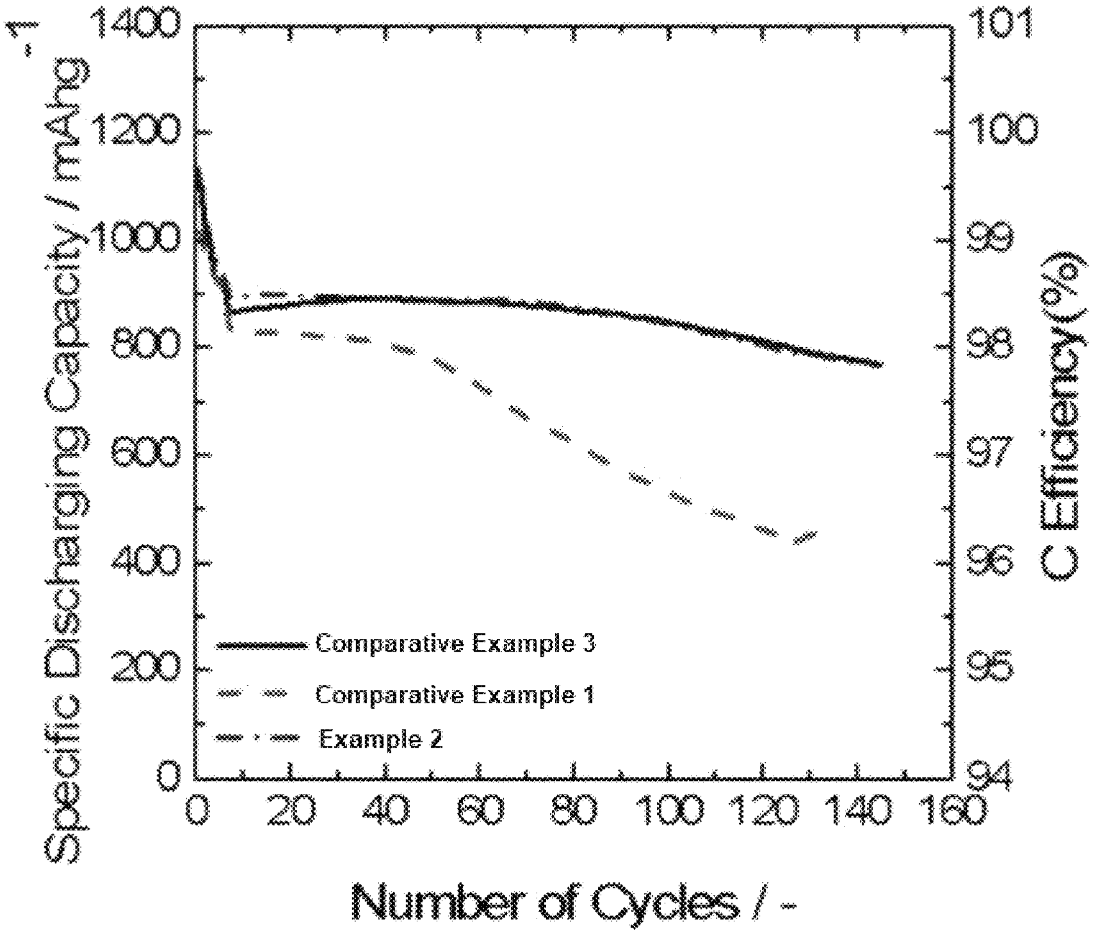

【Figure 6】
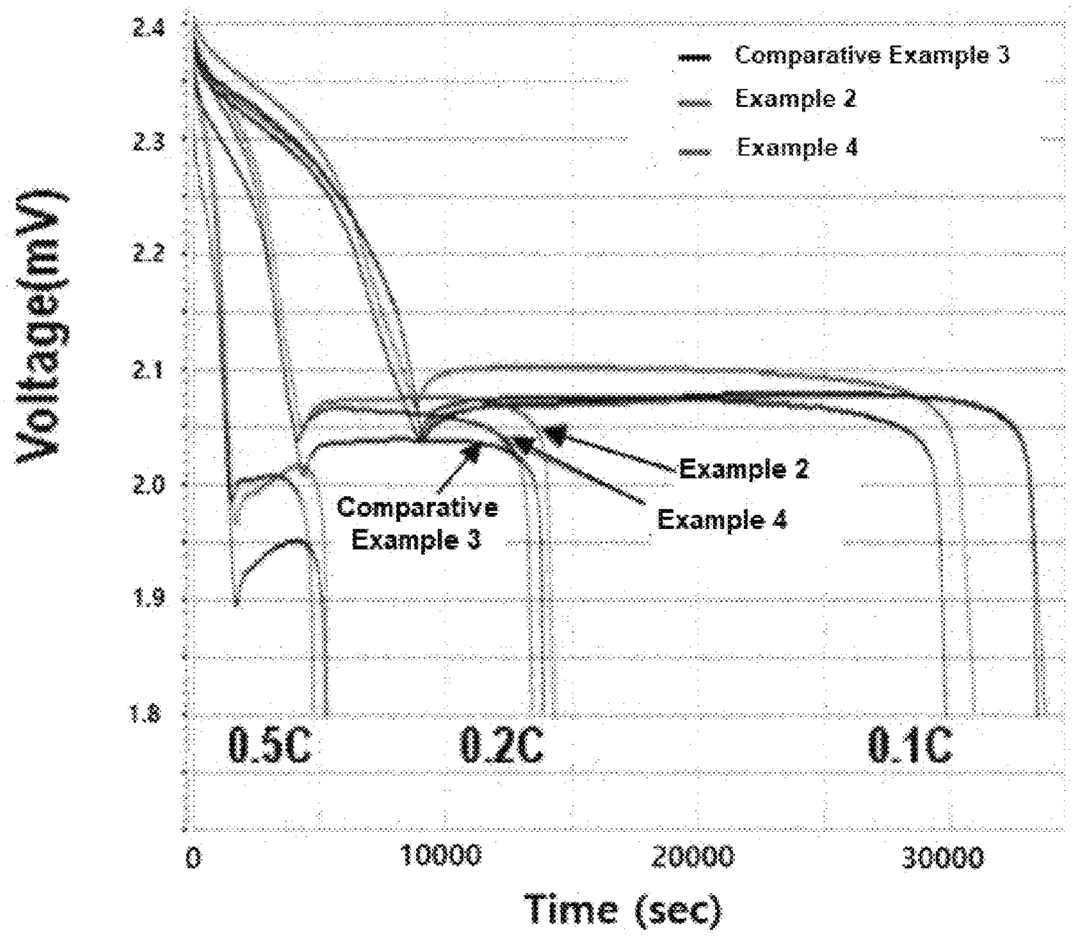

POSITIVE ELECTRODE ADDITIVE FOR LITHIUM SECONDARY BATTERY, POSITIVE ELECTRODE ACTIVE MATERIAL COMPRISING SAME, POSITIVE ELECTRODE, AND LITHIUM SECONDARY BATTERY

CROSS-REFERENCE TO RELATED APPLICATIONS

This application is a National Phase entry pursuant to 35 U.S.C. § 371 of International Application No. PCT/KR2022/000235, filed on Jan. 6, 2022, and claims the benefit of and priority to Korean Patent Application No. 10-2021-0001836, filed on Jan. 7, 2021 and Korean Patent Application No. 10-2021-0004278, filed on Jan. 12, 2021, the disclosures of which are incorporated by reference in their entirety for all purposes as if fully set forth herein.

TECHNICAL FIELD

The present disclosure relates to a positive electrode additive for a lithium secondary battery, and a positive electrode active material, a positive electrode and a lithium secondary battery including the same.

BACKGROUND

Until recently, there have been considerable interests in developing high energy density batteries using lithium as a negative electrode. For example, compared to other electrochemical systems having a lithium-inserted carbon negative electrode and a nickel or cadmium electrode reducing battery energy density by increasing a weight and a volume of a negative electrode with the presence of non-electroactive materials, lithium metal has low weight and high capacity properties, and therefore, has attracted much attention as a negative electrode active material of an electrochemical battery. A lithium metal negative electrode or a negative electrode including mainly lithium metal provides an opportunity to form batteries that are lighter and have higher energy density compared to batteries such as lithium-ion, nickel metal hydride or nickel-cadmium batteries. Such characteristics are highly preferred with batteries for portable electronic devices such as mobile phones and lap-top computers wherein premiums are paid in low weights.

Such types of positive electrode active materials for a lithium battery are known, and the positive electrode active materials include a sulfur-containing positive electrode active material including a sulfur-sulfur bond and accomplish high energy capacity and rechargeability from electrochemical cleavage (reduction) and reformation (oxidation) of the sulfur-sulfur bond.

A lithium-sulfur secondary battery using lithium and an alkali metal as a negative electrode active material and sulfur as a positive electrode active material as described above has theoretical energy density of 2,800 Wh/kg, and theoretical sulfur capacity of 1,675 mAh/g, which are significantly high compared to other battery systems. In addition, with advantages of sulfur being inexpensive due to being abundant in resources and an environmental-friendly material, a lithium-sulfur secondary battery has received attention as an energy source of portable electronic devices.

However, sulfur used as a positive electrode active material of a lithium-sulfur secondary battery is a nonconductor, and therefore, electrons generated by an electrochemical reaction are difficult to migrate. In addition, polysulfide ($Li_2S_8$ to $Li_2S_4$) generated during a charge and discharge process of the lithium-sulfur secondary battery is eluted, and the lithium sulfide ($Li_2S_2$/$Li_2S$) and the sulfur have poor electrical conductivity and have slow kinetics for an electrochemical reaction, which cause problems of declining battery lifetime properties and rate properties.

A research result has been reported that, when introducing benzo[ghi]peryleneimide (BPI) as an additive of a positive electrode in order to improve such problems in a lithium-sulfur secondary battery, the BPI acts as a redox mediator, and is capable of enhancing kinetics of an electrochemical reaction and enhancing performance and lifetime properties of a battery (Laura C. H. Gerber et al.; "Three-Dimensional Growth of $Li_2S$ in Lithium-Sulfur Batteries Promoted by a Redox Mediator"; Nano Lett. 2016, 16, 1, 549-554).

However, the BPI tends to be dissolved in an ether-based solvent or a carbonate-based solvent used in an electrolyte solution of a lithium-sulfur secondary battery, and when the BPI is dissolved in an electrolyte solution, electrons are transferred between a positive electrode and a negative electrode that need to be electrically separated, which causes a problem of declining battery performance by inducing an internal short circuit.

Accordingly, development of an additive that is not dissolved in an electrolyte solution of a lithium secondary battery including a lithium-sulfur secondary battery, and capable of performing a role of a catalyst for a reaction progressed in a positive electrode has been required.

The background description provided herein is for the purpose of generally presenting context of the disclosure. Unless otherwise indicated herein, the materials described in this section are not prior art to the claims in this application and are not admitted to be prior art, or suggestions of the prior art, by inclusion in this section.

DISCLOSURE

Technical Problem

It is an object of the present disclosure to provide a positive electrode additive for a lithium secondary battery capable of performing a role of a catalyst as a redox mediator in a positive electrode without being dissolved in an electrolyte solution for a lithium secondary battery.

It is another object of the present disclosure to provide a positive electrode active material, a positive electrode and a lithium secondary battery including the positive electrode additive for a lithium secondary battery.

Technical Solution

To achieve the above objects, one embodiment of the present disclosure provides a positive electrode additive for a lithium secondary battery represented by the following Formula 1:

<Formula 1>

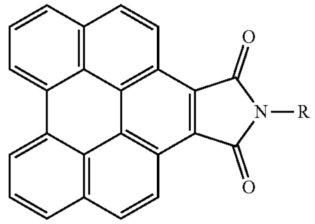

wherein, R is a carbon chain.

Another embodiment of the present disclosure provides a method for preparing a positive electrode additive for a lithium secondary battery including reacting benzoperylene or a derivative thereof and a carbon molecule including an amine group on at least one end.

Another embodiment of the present disclosure provides a positive electrode active material for a lithium secondary battery including a carbon material, and the positive electrode additive on a surface of the carbon material.

Another embodiment of the present disclosure provides a positive electrode for a lithium secondary battery including the positive electrode additive.

Another embodiment of the present disclosure provides a lithium secondary battery including the positive electrode, a negative electrode, a separator interposed therebetween, and an electrolyte solution.

Advantageous Effects

A positive electrode additive for a lithium secondary battery according to the present disclosure is not dissolved in an electrolyte solution, and therefore, a phenomenon of battery performance decline caused by an internal short circuit occurring when a positive electrode additive is dissolved in an electrolyte solution can be prevented.

In addition, the positive electrode additive for a lithium secondary battery exhibits electrochemical activity while being adsorbed to a carbon material included in a positive electrode of a lithium secondary battery, and performs a role of a catalyst for a reaction progressed in the positive electrode, and accordingly, electrochemical activity of the battery may be enhanced.

In addition, the positive electrode additive for a lithium secondary battery exhibits electrochemical activity while being adsorbed to a carbon material included in a positive electrode of a lithium secondary battery, and accordingly, electrochemical activity of the battery may be enhanced.

BRIEF DESCRIPTION OF DRAWINGS

FIG. 1 is a schematic diagram showing raw materials used for synthesizing a positive electrode additive in examples and comparative examples.

FIG. 2 shows graphs each showing an FT-IR (Fourier-transform infrared spectroscopy) measurement result for a mixture solution including a positive electrode additive of each of Example 1 and Comparative Example 1.

FIG. 3 shows photographs showing a color change over time for a mixture solution including a positive electrode additive of Example 1 and a carbon material (MWCNT).

FIG. 4 is a graph showing electrochemical activity of a coin cell depending on the presence or absence of adsorption of a positive electrode additive of Example 1.

FIG. 5 is a graph showing lifetime properties of a coin cell of each of Example 2, and Comparative Examples 1 and 3 depending on the presence or absence of adsorption of a positive electrode additive.

FIG. 6 is a graph showing lifetime properties of a coin cell of each of Example 2, Example 4 and Comparative Example 3 depending on the presence of absence of adsorption of the positive electrode additive.

DETAILED DESCRIPTION

Hereinafter, the present disclosure will be described in more detail to help the understanding of the present disclosure.

Terms or words used in the present specification and the claims are not to be interpreted limitedly to common or dictionary meanings, and shall be interpreted as meanings and concepts corresponding to technical ideas of the present disclosure based on a principle in which the inventors may suitably define the concepts of terms in order to describe the invention in the best possible way.

Positive Electrode Additive for Lithium Secondary Battery

The present disclosure relates to a positive electrode additive for a lithium secondary battery, and relates to a positive electrode additive for a lithium secondary battery adsorbed to a carbon material used in a general positive electrode for a lithium secondary battery and thereby having a physical property of being not dissolved in an electrolyte solution, and having electrochemical activity while being adsorbed to a surface of the carbon material.

In the present disclosure, the positive electrode additive for a lithium secondary battery may be represented by the following Formula 1:

<Formula 1>

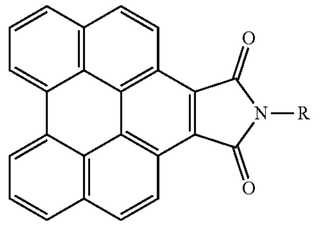

wherein, R is a carbon chain.

The additive of Formula 1 has a structure in which a carbon chain is introduced to benzo[ghi]peryleneimide (BPI). The carbon chain is not particularly limited in the form, and may be, for example, a linear, cyclic or branched carbon chain.

In addition, when the carbon chain is a linear carbon chain, an adsorption process for a carbon material may be readily conducted compared to when the carbon chain is a cyclic or branched carbon chain, and process efficiency may be enhanced. For example, the linear carbon chain may be an aliphatic carbon chain.

The BPI is an imide compound synthesized by dehydration condensation of molecules including benzoperylene anhydride (BPA) and amine, and used as a positive electrode additive for a lithium secondary battery. However, since the BPI has a property of being dissolved in an electrolyte solution, electrons are transferred between a positive electrode and a negative electrode that need to be electrically separated while being dissolved in the electrolyte solution, which causes a problem of declining battery performance by inducing an internal short circuit.

However, when a carbon chain is introduced to the BPI as in Formula 1 above, it is not dissolved in an electrolyte solution since a carbon chain is not dissolved well in a common electrolyte solution solvent. Herein, the electrolyte solution means an electrolyte solution for a lithium secondary battery, and for example, may mean an electrolyte solution including a carbonate-based solvent and/or an ether-based solvent.

When the number of carbon atoms is small in the carbon chain, solubility for an electrolyte solution is not controlled, making it difficult to provide a function to prevent carbon atoms from being dissolved in an electrolyte solution, and when the number of carbon atoms is large, the ratio of the benzoperylene anhydride (BPA) capable of participating in an electrochemical reaction relatively decreases, which may reduce the effect per mass of the additive, and may also unnecessarily increase a battery weight. Accordingly, R may be an alkyl group having 8 to 12 carbon atoms.

In addition, when the additive of Formula 1 includes an ether chain or the like instead of a carbon chain, affinity with an electrolyte solution solvent having polarity is enhanced by an atom such as oxygen having high electronegativity, and therefore, the additive is readily dissolved in an electrolyte solution leading to electron transfer between a positive electrode and a negative electrode, and battery performance may decline by causing an internal short circuit.

Method for Preparing Positive Electrode Additive for Lithium Secondary Battery

The present disclosure also relates to a method for preparing a positive electrode additive for a lithium secondary battery, and the method may include reacting (i) benzoperylene or a derivative thereof, and (ii) a carbon molecule including an amine group on at least one end.

In the present disclosure, the benzoperylene derivative may be benzoperylene anhydride (BPA), amine group-containing benzoperylene or carboxyl group-containing benzoperylene, and considering reactivity with a carbon molecule, the benzoperylene derivative may be preferably benzoperylene anhydride (BPA).

In addition, in the present disclosure, the carbon molecule including an amine group on at least one end may be an alkylamine having 8 to 12 carbon atoms. For example, the alkylamine having 8 to 12 carbon atoms may be octylamine ($C_8H_{19}N$), 1-aminodecane (C10), or dodecylamine (C12).

In addition, the reaction may be a dehydration condensation reaction including steps of dissolving the reaction materials in an organic solvent, refluxing the result at a temperature of 100 to 200° C., and cooling the result. Herein, the organic solvent is not particularly limited as long as it is an organic solvent that may be generally used in a positive electrode reaction of a lithium secondary battery, and examples thereof may include DMF (dimethylformamide).

The reaction temperature may be 100° C. or higher, 120° C. or higher, or 140° C. or higher, and 160° C. or lower, 170° C. or lower, or 200° C. or lower. When the reaction temperature is less than 100° C., the reaction rate is low and a target compound may not be obtained, and when the reaction temperature exceeds 200° C. or significantly higher than a boiling point of the solvent, bubbles are generated by vaporization, and experimental apparatuses may be damaged.

In addition, the reflux may be conducted for 5 to 30 hours considering the degree of the additive of Formula 1 being sufficiently synthesized, and specifically, the reflux may be conducted for 5 hours or longer or 10 hours or longer, or conducted for 20 hours or shorter or 30 hours or shorter. When the reflux time is less than 10 hours, the reaction is not finished, and thus a target product may not be obtained, and when the reflux time exceeds 30 hours, an overreaction occurs, and process efficiency may decrease.

In addition, the cooling may be cooling to room temperature, and herein, the room temperature may be 20° C. or higher or 23° C. higher, and 27° C. or lower or 30° C. or lower, and for example, may be 25° C. When the cooling temperature is less than 20° C., the cooling time increases resulting in an unnecessarily long process time, and when the cooling temperature exceeds 30° C., the cooling is not sufficient, and thus the yield in the step of precipitation may be reduced.

In addition, after the cooling, a step of adding methanol and stirring the result so as to precipitate the reaction product in the solution may be further included. The stirring time may be from 30 minutes to 3 hours. For example, the stirring time may be 30 minutes or longer or 1 hour or longer, and may be 2 hours or shorter or 3 hours or shorter. When the stirring time is less than 30 minutes, the time for precipitation is not sufficiently secured, reducing a yield, and when the stirring time exceeds 3 hours, process efficiency may decrease.

In addition, after the step of stirring, a step of vacuum filtering and washing the mixture may be further included, and purity may be enhanced.

Positive Electrode Active Material for Lithium Secondary Battery

In the present disclosure, the positive electrode active material includes a carbon material, and a positive electrode additive represented by the following Formula 1 on a surface of the carbon material:

<Formula 1>

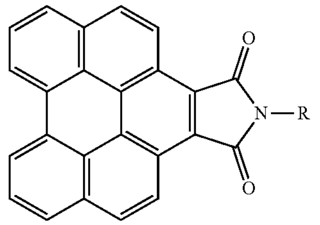

wherein, R is a carbon chain.

The positive electrode additive represented by Formula 1 is the same as described above.

In addition, the carbon material is a porous carbon material, and the positive electrode additive may be adsorption-bonded to any one or more of an outer surface and an inner surface of the porous carbon material.

In addition, in the positive electrode active material for a lithium secondary battery of the present disclosure, the additive may be included in 1 to 15% by weight with respect to a total weight of the carbon material and the additive. When the additive content is less than 1% by weight, the effect obtained from including the additive becomes insignificant, and when exceeding 15% by weight, the additive content exceeds an adsorption limit of the carbon material, and some of the additives in an electrolyte solution is eluted, causing self-discharge, or energy density of a battery may be reduced by an increase in the weight.

In the present disclosure, a positive electrode active material layer may include, together with the positive electrode active material described above, a conductor and a binder.

The conductor is used for providing conductivity to an electrode, and, in the formed battery, may be used without particular limit as long as it has electron conductivity without causing chemical changes. Specific examples thereof may include graphite such as natural graphite or artificial graphite; carbon-based materials such as carbon black, acetylene black, Ketjen black, channel black, furnace black, lamp black, thermal black or carbon fiber; metal powders such as copper, nickel, aluminum, or silver or metal fibers; conductive whiskers such as zinc oxide or potassium titanate; conductive metal oxides such as titanium oxide; conductive polymers such as polyphenylene derivatives, or the like, and among these, one type alone or a mixture of two or more types may be used. The conductor may be commonly included in to 30% by weight with respect to a total weight of the positive electrode active material layer.

The binder performs a role of enhancing adhesion between particles of the positive electrode active material and adhesive strength between the positive electrode active material and a positive electrode current collector. Specific examples thereof may include polyvinylidene fluoride (PVDF), a vinylidene fluoride-hexafluoropropylene copolymer (PVDF-co-HFP), polyvinyl alcohol, polyacrylonitrile, carboxymethyl cellulose (CMC), starch, hydroxypropyl cellulose, regenerated cellulose, polyvinyl pyrrolidone, tetrafluoroethylene, polyethylene, polypropylene, an ethylene-propylene-diene polymer (EPDM), a sulfonated-EPDM, styrene-butadiene rubber (SBR), fluorine rubber, various copolymers thereof, or the like, and among these, one type alone or a mixture of two or more types may be used. The binder may be included in 1 to 30% by weight with respect to a total weight of the positive electrode active material layer.

In the positive electrode active material for a lithium secondary battery of the present disclosure, the positive electrode active material may further include sulfur. Specifically, in the positive electrode active material for a lithium secondary battery of the present disclosure, a sulfur-carbon composite obtained by compositing the above-described additive-adsorbed carbon material with sulfur powder may be prepared. A method for preparing the sulfur-carbon composite is not particularly limited, and methods for preparing a sulfur-carbon composite commonly used in the art may be used.

For example, the sulfur-carbon composite may be prepared using a melt-diffusion method. The melt-diffusion method is a preparation method of penetrating sulfur into carbon particles by melting sulfur through heating. Herein, the heat treatment may include various direct or indirect heating methods.

The sulfur-carbon composite according to the present disclosure may include (S1) mixing sulfur and carbon; and heat treating the mixture of sulfur and carbon formed in the step (S1). Specifically, a temperature during the heat treatment is from 100 to 200° C., preferably from 110 to 190° C., and more preferably from 120 to 180° C., and the heat treatment may use the melt-diffusion method. When the temperature is less than the above range, the sulfur-carbon composite itself may not be prepared since the process of dissolving and permeating sulfur into carbon does not proceed, and when the temperature excesses the above range, the rate of loss increases due to vaporization of the sulfur and the sulfur-carbon composite is denatured, and thus an effect of improving battery performance may be insignificant when used as a positive electrode material of a lithium secondary battery.

In addition, when including sulfur and a carbon material in the positive electrode active material for a lithium secondary battery of the present disclosure, a weight ratio of the sulfur and a total weight of the carbon material and the additive may be from 1:1 to 1:0.1, and preferably from 1:0.5 to 1:0.2. When the sulfur ratio is higher than the above range, resistance of a cell may increase since conductivity by carbon is insufficient, and when the sulfur ratio is lower than the above range, the weight ratio of the sulfur is excessively low, which excessively reduces energy density of a battery.

Positive Electrode for Lithium Secondary Battery

The present disclosure also relates to a positive electrode for a lithium secondary battery including the positive electrode active material.

Preferably, the additive of Formula 1 included in the positive electrode is not dissolved in a carbonate-based solvent and/or an ether-based solvent generally used as an electrolyte solution of a lithium secondary battery, and therefore, may be suitable as a positive electrode of a lithium-sulfur secondary battery including a sulfur-carbon composite as a positive electrode active material.

The positive electrode active material for a lithium secondary battery of the present disclosure may be obtained by adsorbing the additive of Formula 1 on a surface of the carbon material included in the positive electrode. Due to strong bonding strength by the adsorption, the additive of Formula 1 may not be dissolved in an electrolyte solution even when driving a battery, and accordingly, a phenomenon such as a battery short circuit caused by the additive of Formula 1 being dissolved in an electrolyte solution may be prevented. In addition, since the additive of Formula 1 may be attached to a surface of the carbon material without chemical bonding, chemical/electrochemical intervention that may occur when adding other chemical materials necessary for chemical bonding may be prevented. In addition, since the adsorption occurs fast, the reaction of being attached to the surface may be completed within few minutes.

In the present disclosure, the additive of Formula 1 above and the carbon material (including the additive) may have a weight ratio of 0.01:1 to 0.15:1, and specifically, the weight ratio may be 0.01:1 or greater, 0.02:1 or greater, 0.03:1 or greater, or 0.04:1 or greater, and 0.15:1 or lower, 0.09:1 or lower, 0.08:1 or lower, or 0.06:1 or lower. When the weight ratio is less than 0.01:1, significant changes may not occur since the content of the additive of Formula 1 is small, and when exceeding 0.15:1, the content of the additive exceeds an adsorption limit of the carbon material, and thus some of the additives in an electrolyte solution is eluted, causing self-discharge, or energy density of a battery may be reduced by an increase in the weight.

Lithium Secondary Battery

The present disclosure also relates to a lithium secondary battery including a positive electrode, a negative electrode, a separator interposed therebetween, and an electrolyte solution, and the positive electrode includes the positive electrode active material including the additive of Formula 1. The additive of Formula 1 may be included in a positive electrode active material layer and/or a negative electrode active material layer as describe later.

The electrolyte solution of the present disclosure may include an organic solvent and a lithium salt.

The organic solvent may be used without particular limit as long as it is capable of performing a role of a medium through which ions involved in an electrochemical reaction of a battery migrate, and may be used to preferably include one or more types selected from among ether-based solvents and carbonate-based solvents.

Specifically, as the organic solvent, ester-based solvents such as methyl acetate, ethyl acetate, γ-butyrolactone, and ε-caprolactone; ether-based solvents such as dibutyl ether or tetrahydrofuran; ketone-based solvents such as cyclohexanone; aromatic hydrocarbon-based solvents such as benzene and fluorobenzene; carbonate-based solvents such as dimethyl carbonate (DMC), diethyl carbonate (DEC), methyl ethyl carbonate (MEC), ethyl methyl carbonate (EMC), ethylene carbonate (EC), and propylene carbonate (PC); alcohol-based solvents such as ethyl alcohol and isopropyl alcohol; nitriles such as R—CN (R is a C2 to C20 linear, branched, or cyclic-structured hydrocarbon group, and may include a double bond aromatic ring or ether bond);

amides such as dimethylformamide; dioxolanes such as 1,3-dioxolane; sulfolanes, or the like may be used. Among these, carbonate-based solvents are preferred, and a mixture of a cyclic carbonate (for example, ethylene carbonate, propylene carbonate or the like) having high ion conductivity and high dielectric constant capable of enhancing charge and discharge performance of a battery, and a low-viscosity linear carbonate-based compound (for example, ethyl methyl carbonate, dimethyl carbonate, diethyl carbonate or the like) is more preferred. In this case, performance of the electrolyte solution is superior when mixing the cyclic carbonate and the linear carbonate in a volume ratio of approximately 1:1 to approximately 1:9.

The lithium salt may be used without particular limit as long as it is a compound capable of providing lithium ions used in a lithium secondary battery. Specifically, as the lithium salt, $LiPF_6$, $LiClO_4$, $LiAsF_6$, $LiBF_4$, $LiSbF_6$, $LiAlO_4$, $LiAlCl_4$, $LiCF_3SO_3$, $LiC_4F_9SO_3$, $LiN(C_2F_5SO_3)_2$, $LiN(C_2F_5SO_2)_2$, $LiN(CF_3SO_2)_2$. LiCl, LiI, $LiB(C_2O_4)_2$ or the like may be used. The concentration of the lithium salt is preferably used in a range of 0.1 M to 2.0 M. When the lithium salt concentration is included in the above-mentioned range, the electrolyte has proper conductivity and viscosity leading to excellent electrolyte performance, and lithium ions may effectively migrate.

With the purpose of enhancing lifetime properties of a battery, suppressing a decrease in battery capacity, enhancing discharging capacity of a battery, and the like, the electrolyte may further include, in addition to the above-described electrolyte components, one or more types of additives such as, for example, a haloalkylenecarbonate-based compound such as difluoroethylene carbonate, pyridine, triethylphosphite, triethanolamine, cyclic ether, ethylenediamine, n-glyme, hexaphosphoric acid triamide, a nitrobenzene derivative, sulfur, a quinoneimine dye, N-substituted oxazolidinone, N,N-substituted imidazolidine, ethylene glycol dialkyl ether, ammonium salt, pyrrole, 2-methoxyethanol or aluminum trichloride. Herein, the additive may be included in 0.1 to 5% by weight with respect to a total weight of the electrolyte.

In the present disclosure, the positive electrode includes a positive electrode current collector and a positive electrode active material layer formed on the positive electrode current collector and including the positive electrode active material described above.

In the positive electrode, the positive electrode current collector is not particularly limited as long as it has conductivity without inducing chemical changes to a battery, and for example, stainless steel, aluminum, nickel, titanium, baked carbon, or aluminum or stainless steel of which surface is treated with carbon, nickel, titanium, silver or the like, may be used. In addition, the positive electrode current collector may commonly have a thickness of 3 to 500 μm, and micro-unevenness may be formed on the positive electrode current collector surface to increase adhesive strength with the positive electrode active material. The positive electrode current collector may be used in various forms such as, for example, films, sheets, foil, nets, porous bodies, foams, and non-woven fabrics.

The positive electrode may be prepared using a common positive electrode preparation method except that the positive electrode active material described above is used. Specifically, a composition for forming a positive electrode active material layer including the positive electrode active material described above, and, optionally, a binder and a conductor is coated on the positive electrode current collector, and then dried and rolled to prepare the positive electrode. Herein, each type and content of the positive electrode active material, the binder, and the conductor are as described above.

As the solvent, solvents generally used in the art may be used, and examples thereof may include dimethyl sulfoxide (DMSO), isopropyl alcohol, N-methylpyrrolidone (NMP), acetone, water or the like, and among these, one type alone or a mixture of two or more types may be used. The amount of the solvent used is sufficient as long as, considering the coating thickness of the slurry and the preparation yield, the positive electrode active material, the conductor, and the binder are dissolved or dispersed, and viscosity is obtained enough to achieve excellent thickness uniformity when coating for preparing the positive electrode afterward.

As another method, the positive electrode may also be prepared by casting the composition for forming a positive electrode active material layer on a separate support, and laminating a film obtained by peeling from this support on the positive electrode current collector.

In the present disclosure, the negative electrode includes a negative electrode current collector, and a negative electrode active material layer disposed on the negative electrode current collector.

The negative electrode active material layer optionally includes a binder and a conductor together with the negative electrode active material.

As the negative electrode active material, compounds capable of reversibly intercalating or deintercalating lithium may be used. Specific examples thereof may include carbon materials such as artificial graphite, natural graphite, graphitized carbon fiber, or amorphous carbon; metal compounds capable of alloying with lithium such as Si, Al, Sn, Pb, Zn, Bi, In, Mg, Ga, Cd, Si alloys, Sn alloys, or Al alloys; metal oxides capable of doping and dedoping lithium such as $SiO_\beta$ ($0<\beta<2$), $SnO_2$, vanadium oxides, or lithium vanadium oxides; or composites including the metal compounds and the carbon materials such as Si—C composites or Sn—C composites, or the like, and among these, any one or a mixture of two or more may be used. In addition, a metal lithium thin film may also be used as the negative electrode active material. In addition, as the carbon material, low-crystalline carbon, high-crystalline carbon and the like may all be used. Representative examples of the low-crystalline carbon may include soft carbon and hard carbon, and representative examples of the high crystalline carbon may include high temperature baked carbon such as amorphous, plate-type, scaly, spherical or fibrous natural graphite or artificial graphite, Kish graphite, pyrolytic carbon, mesophase pitch based carbon fiber, meso-carbon microbeads, mesophase pitches, and petroleum or coal tar pitch derived cokes.

The binder, the conductor, and the negative electrode current collector may be selected with reference to the constitutions in the positive electrode described above, but are not limited thereto. In addition, the method of forming the negative electrode active material layer on the negative electrode current collector may include known coating methods as in the positive electrode, and is not particularly limited.

In the present disclosure, the separator separates the negative electrode and the positive electrode and provides a migration passage for lithium ions, and those commonly used as a separator in a lithium secondary battery may be used without particular limit, and those having an excellent electrolyte solution moisture-containing ability while having low resistance for ion migration of the electrolyte are particularly preferred. Specifically, porous polymer films, for example, porous polymer films prepared with a polyolefin-based polymer such as an ethylene homopolymer, a propylene homopolymer, an ethylene/butene copolymer, an ethylene/hexene copolymer, and an ethylene/methacrylate copolymer, or a laminated structure of two or more layers thereof may be used. In addition, common porous non-woven fabrics, for example, non-woven fabrics made of high melting point glass fiber, polyethylene terephthalate fiber and the like may also be used. In addition, a coated separator including a ceramic component or a polymer material may also be used in order to secure heat resistance or mechanical strength, and a single layer or multilayer structure may be selectively used.

Hereinafter, preferred examples are provided in order to illuminate the present disclosure, however, the following examples are for illustrative purposes only, and it will be obvious to those skilled in the art that various changes and modifications may be made within the category and technical ideas of the present disclosure, and such changes and modifications also fall within the scope of the appended claims.

FIG. 1 is a schematic diagram showing raw materials used for synthesizing a positive electrode additive in examples and comparative examples, and in the following examples and comparative examples, raw materials as shown in FIG. 1 were used to synthesize the additive.

Preparation Example 1: Preparation of Benzoperylene Anhydride (BPA)

In a three-neck flask, a glass topper, a thermos-couple, and a reflux condenser were each installed and placed in a heating mantle.

Maleic anhydride of 123.0 g was introduced thereto and dissolved at 75° C., and after adding perylene of 8.04 g thereto, the result was heated to 240° C.

Chloranil of 16.5 g was introduced thereto, the result was refluxed for 10 minutes, then cooled to 140° C., and xylene of 160 ml heated to 60° C. was added thereto to obtain a mixture.

The mixture was cooled to 90° C. and then filtered. The filtered mixture was introduced to an ethyl acetate/chloroform (2:1 (v/v)) solution, and purified by repeating washing processes of heating to 65° C. and filtering twice.

After that, the purified mixture was vacuum dried at 70° C. to prepare BPA.

Example 1

(1) Preparation of Positive Electrode Additive

BPA of 8 g prepared in Preparation Example 1 and octylamine (C8) of 45 mmol were introduced, refluxed overnight at 160° C., and then cooled to room temperature to obtain a synthesized compound.

Methanol of 300 ml was introduced to the compound, and the mixture was stirred for 1 hour at room temperature.

After that, the stirred mixture was vacuum filtered, then washed several times with methanol, and dried to prepare a positive electrode additive of a lithium secondary battery (C8 A-BPI).

(2) Preparation of Positive Electrode Active Material

The additive prepared in Preparation Example 1 and multi-walled carbon nanotubes (MWCNT, CNano company) as a carbon material were mixed in a tetrahydrofuran (THF) solvent. After that, the mixture was dried for 1 day at 80° C. to prepare a positive electrode active material in a form of MWCNT powder to which the additive of Preparation Example 1 above was adsorbed. Herein, the additive and the carbon material were mixed so that the additive was included in 4 parts by weight with respect to 100 parts by weight of the MWCNT powder based on the finally produced MWCNT powder.

(3) Manufacture of Positive Electrode and Coin Cell

The MWCNT powder to which the additive of Preparation Example 1 was adsorbed, the positive electrode active material prepared above, and a carboxymethyl cellulose (CMC) binder were mixed in parts by weight of 96:4 to prepare aqueous slurry. The aqueous slurry was coated on aluminum foil and dried, and punched at 14 pi to be employed as a reference electrode, and with a lithium electrode employed as a counter electrode, a coin cell was manufactured. When manufacturing the coin cell, a polyethylene separator (16 μm, Celgard) was used as a separator, and as an electrolyte solution, an electrolyte solution of LiTFSI 1 M in a mixed solvent (1:1 (v/v)) of DOL and DME was used.

Example 2

(1) Preparation of Positive Electrode Additive

A positive electrode additive (C10 A-BPI) of a lithium secondary battery was prepared in the same manner as in Example 1 except that 1-aminodecane (C10) was used instead of octylamine.

(2) Preparation of Positive Electrode Active Material

After that, sulfur and MWCNT powder to which the positive electrode additive (C10 A-BPI) was adsorbed in 4 parts by weight with respect to 100 parts by weight of the MWCNT as in Example 1 above were mixed in parts by weight of 1:0.33, and the result was heat treated for 1 hour at 150° C. to prepare sulfur-carbon composite powder that is a positive electrode active material.

(3) Manufacture of Positive Electrode and Coin Cell

The sulfur-carbon composite powder and a carboxymethyl cellulose (CMC) binder were mixed in parts by weight of 96:4 to prepare aqueous slurry. The aqueous slurry was coated on aluminum foil and dried, and punched at 14 pi to be employed as a reference electrode, and with a lithium electrode employed as a counter electrode, a coin cell was manufactured. When manufacturing the coin cell, a polyethylene separator (16 μm, Celgard) was used as a separator, and as an electrolyte solution, an electrolyte solution of LiTFSI 1 M in a mixed solvent (1:1 (v/v)) of DOL and DME was used.

Example 3

A positive electrode additive (C12 A-BPI) of a lithium secondary battery, a positive electrode active material and a coin cell-type lithium-sulfur secondary battery were prepared in the same manner as in Example 1 except that dodecylamine (C12) was used instead of octylamine.

Example 4

A positive electrode active material and a coin cell-type lithium-sulfur secondary battery were prepared in the same manner as in Example 2 except that, as the positive electrode active material, MWCNT powder to which the positive electrode additive (C10 A-BPI) of Example 2 was adsorbed in 8 parts by weight with respect to 100 parts by weight of the MWCNT powder was used.

Comparative Example 1

A positive electrode additive of a lithium secondary battery, a positive electrode active material, a positive electrode, and a coin cell were prepared in the same manner as in Example 1 except that tetraethylene glycol monoamine was used instead of octylamine (C8).

Comparative Example 2

A coin cell was manufactured in the same manner as in Example 1 except that general MWCNT powder to which no additive was adsorbed was used as the positive electrode active material.

Comparative Example 3

A coin cell was manufactured in the same manner as in Example 2 except that general MWCNT powder to which no additive was adsorbed was used as the positive electrode active material.

Experimental Example 1: Solubility Experiment on Electrolyte Solution Solvent for Lithium Secondary Battery A solubility experiment on whether the additive prepared in each of Example 1 and Comparative Example 1 was dissolved in an electrolyte solution solvent was conducted (Example 1: C8 linear carbon chain, Comparative Example 1: C8 linear ether chain).

As the solvent for the solubility experiment, dimethoxyethane (DME) generally used in a lithium-sulfur secondary battery was used.

The positive electrode additive of 0.1 g of each of Example 1 and Comparative Example 1 was introduced to a dimethoxyethane solvent of 10 g, and after mixing the mixture for 1 day, FT-IR (Fourier-transform infrared spectroscopy) measurement was conducted thereon to check the presence of a solute in the mixture solution. Herein, the FT-IR was measured using a Nicolet iS5 (Thermo Fisher Scientific Solutions LLC).

FIG. 2 shows graphs each showing the FT-IR measurement result for the mixture solution including the positive electrode additive of each of Example 1 and Comparative Example 1.

As shown in FIG. 2, it was identified that a C═O peak that is a characteristic of the positive electrode additive material did not appear in the mixture solution including the positive electrode additive of Example 1, and a C═O peak appeared in the mixture solution including the positive electrode additive of Comparative Example 1.

From such results, it can be seen that the additive of Example 1 was not dissolved in the DME solvent, and the additive of Comparative Example 1 was dissolved in the DME solvent.

Experimental Example 2: Carbon Absorptivity Experiment

A carbon absorptivity experiment on whether the positive electrode additive of a lithium secondary battery prepared in Example 1 shows absorptivity for a carbon material was conducted.

The positive electrode additive of a lithium secondary battery prepared in Example 1 and a carbon material were mixed in a tetrahydrofuran (THF) solvent, and the mixture solution was visually observed immediately after the mixing and after 1 day after the mixing. Herein, multi-walled carbon nanotubes (MWCNT, CNano company) were used as the carbon material. In addition, the additive and the carbon material were mixed to be 1% by weight and 25% by weight, respectively, based on the total weight of the mixture solution (the additive and the carbon material had a weight ratio of 0.04:1).

FIG. 3 shows photographs showing a color change over time for the mixture solution including the positive electrode additive of Example 1 and the carbon material (MWCNT).

As shown in FIG. 3, it was identified that the mixture solution showed a yellow color immediately after mixing the positive electrode additive of Example 1 and the MWCNT in the THF solvent (before adsorption), whereas the yellow color disappeared when 1 day had passed after the mixing (after adsorption).

From such results, it was seen that, in the mixture solution including the additive of Example 1 and the MWCNT that is a carbon material, the additive of Example 1 was adsorbed to the carbon material and was not dissolved in the solvent.

Experimental Example 3: Experiment on Relation with Electrochemical Activity of Battery For the coin cell including the positive electrode active material prepared in each of Example 1 and Comparative Example 2, an experiment on electrochemical activity was conducted.

The positive electrode active material of Example 1 is MWCNT powder to which the positive electrode additive (C8 A-BPI) prepared using octylamine (C8) as a raw material was adsorbed, and the positive electrode active material of Comparative Example 1 is general MWCNT powder to which no positive electrode additive was adsorbed.

The coin cell of each of Example 1 and Comparative Example 2 went back and forth three times in the 1.8 to 2.9 V section at a rate of 10 mV/sec, and a voltage change-dependent current was measured at the third round-trip (VMP3, Biologic).

FIG. 4 is a graph showing electrochemical activity of the coin cell depending on the presence or absence of adsorption of the positive electrode additive of Example 1.

As shown in FIG. 4, it was identified that the coin cell including MWCNT to which the positive electrode additive of Example 1 was adsorbed had electrochemical activity in a 1.8 to 2.5 V range, a general driving range of a lithium-sulfur secondary battery.

From such results, it can be seen that the positive electrode additive of Example 1 will enhance electrochemical activity of a lithium secondary battery including a lithium-sulfur secondary battery.

Experimental Example 4: Identification of Lifetime Properties

The coin cell of each of Example 2 and Comparative Examples 1 and 3 was charged and discharged three times in a 1.8 to 2.5 V range with a constant current of 0.1 C, and battery capacity was measured under a condition of continuously charging and discharging in the same voltage range with a constant current of 0.2 C/0.5 C (charge/discharge). The results are shown in FIG. 5 (potentiostat of PNE Company was used).

As shown in FIG. 5, it was identified that, whereas Example 2 had no problem of decline in the lifetime, the lifetime rapidly declined in Comparative Example 1 as the catalyst was eluted in the electrolyte solution.

Experimental Example 4: Identification of Discharging Capacity-Dependent Change in Voltage for Each Discharge Rate For the coin cell of each of Example 2, Example 4, and Comparative Example 3, a discharging capacity-dependent change in the voltage for each discharge rate was measured and lifetime properties were compared. The results are shown in FIG. 6.

As shown in FIG. 6, it could be seen that Example 2 and Example 4 had an increased discharge voltage compared to Comparative Example 3.

Hereinbefore, the present disclosure has been described with reference to limited examples and drawings, however, the present disclosure is not limited thereto, and various changes and modifications may be made within technical ideas of the present disclosure and range of equivalents of the scope of claims to describe below by those skilled in the art.

The invention claimed is:

1. A positive electrode additive for a lithium secondary battery represented by the following Formula 1:

<Formula 1>

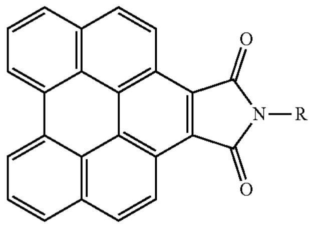

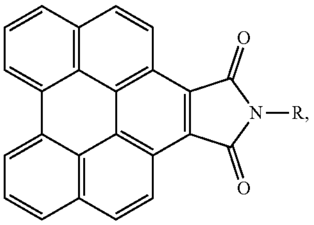

wherein, R is a linear alkyl group having 8 to 11 carbon atoms.

2. A method for preparing the positive electrode additive for the lithium secondary battery of claim 1, comprising:

reacting (i) benzoperylene or a derivative thereof and (ii) a carbon molecule including an amine group on at least one end.

3. The method for preparing a positive electrode additive for a lithium secondary battery of claim 2, wherein the benzoperylene derivative is benzoperylene anhydride (BPA), amine group-containing benzoperylene, or carboxyl group-containing benzoperylene.

4. The method for preparing a positive electrode additive for a lithium secondary battery of claim 2, wherein the carbon molecule including an amine group on at least one end is an alkylamine having 8 to 12 carbon atoms.

5. The method for preparing a positive electrode additive for a lithium secondary battery of claim 2, wherein the reaction is a dehydration condensation reaction including refluxing at a temperature of 100° C. to 200° C. and then cooling.

6. A positive electrode active material for a lithium secondary battery, comprising:

a carbon material; and the positive electrode additive of claim 1 on a surface of the carbon material.

7. The positive electrode active material for a lithium secondary battery of claim 6, wherein the carbon material is a porous carbon material, and the positive electrode additive is adsorption-bonded to any one or more of an outer surface and an inner surface of the porous carbon material.

8. The positive electrode active material for a lithium secondary battery of claim 6, wherein the positive electrode additive is included in an amount of 1 to 15% by weight based on a total weight of the carbon material and the positive electrode additive.

9. The positive electrode active material for a lithium secondary battery of claim 6, further comprising sulfur.

10. The positive electrode active material for a lithium secondary battery of claim 9, wherein a weight ratio of the sulfur to the total weight of the carbon material and the positive electrode additive is from 1:1 to 1:0.1.

11. A positive electrode for a lithium secondary battery, comprising the positive electrode active material of claim 6.

12. A lithium secondary battery comprising:

the positive electrode of claim 11;

a negative electrode;

a separator interposed therebetween; and an electrolyte solution.

13. The lithium secondary battery of claim 12, wherein the electrolyte solution comprises one or more types of ether-based solvents and carbonate-based solvents.

* * * * *